US00PP19598P2

(12) United States Plant Patent
Kordes

(10) Patent No.: US PP19,598 P2
(45) Date of Patent: Dec. 30, 2008

(54) MINIATURE ROSE PLANT NAMED 'KORHEDANI'

(50) Latin Name: *Rosa hybrida*
Varietal Denomination: KORhedani

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 9 days.

(21) Appl. No.: 11/787,185

(22) Filed: Apr. 13, 2007

(51) Int. Cl.
*A01H 5/00* (2006.01)

(52) U.S. Cl. ..... Plt./122
(58) Field of Classification Search ..... Plt./122
See application file for complete search history.

(56) References Cited

PUBLICATIONS

QZ (CPVO) Application #2006/0364 Apr. 15, 2006.

*Primary Examiner*—Annette H Para
*Assistant Examiner*—S. B. McCormick-Ewoldt

(57) ABSTRACT

A new and distinct variety of miniature rose with long lasting, novel red flowers, and dark green and attractive foliage. It exhibits upright, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORhedani'.

BACKGROUND OF THE INVENTION

The new variety of miniature rose plant of the present invention originated from a controlled crossing in a breeding program between an 'un-named seedling', and 'KORpolare', U.S. Plant patent application Ser. No. 11/704,616.

The resulting seeds were planted in a glasshouse during the following winter, subsequently germinated and grew. The resulting seedlings exhibited distinctive physical and biological characteristics. The new rose plant was selected in as a single plant from the seedling beds due to its superior characteristics and asexually propagated for further evaluation. This new and distinctive rose variety is named 'KORhedani'.

SUMMARY OF THE INVENTION

GENUS, SPECIES and VARIETY DENOMINATION

The botanical classification of the new rose plant is *Rosa hybrida.* 'KORhedani'.

BACKGROUND OF THE INVENTION

The new variety of miniature rose plant of the present invention originated from a controlled crossing in a breeding program between an 'un-named seedling', and 'KORpolare', an un-patented rose variety from the same breeder.

The hybridization, seed production, seed germination, seedling selection, and subsequent propagations were conducted in controlled greenhouse environments. The new rose plant was selected as a single plant from the seedling beds due to its superior characteristics and asexually propagated for further evaluation. This new and distinctive miniature rose variety is named 'KORhedani'.

SUMMARY OF THE INVENTION

The new rose plant may be distinguished from its seed parent, an 'un-named seedling', by the following combination of characteristics:

1. 'KORhedani' has dark red flowers while the seed parent has salmon pink flowers; and
2. 'KORhedani' has semi-glossy foliage while the seed parent has matte foliage.

The new rose plant may be distinguished from its pollen parent, 'KORpolare' by the following combination of characteristics:

1. 'KORhedani' has multiple flowers per stem, while the pollen parent generally only has one flower per stem; and
2. The pollen parent has larger flowers than 'KORhedani'.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers;

This combination of qualities is not present in prior rose cultivars. These objectives have been substantially achieved and in that distinguish 'KORhedani' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORhedani' was selected in May, 2003 from the seedling beds to be asexually propagated for further evaluation. The first asexual reproduction of 'KORhedani' was done by rooting softwood cuttings in July, 2003 at the Rosa-Danica Nursery in Odense, Denmark.

This initial and other subsequent propagations conducted in controlled environment show that the foregoing and all other characteristics of 'KORhedani' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORhedani'. Illustrated in SHEET ONE are flower buds, an open bloom, detached petals, floral parts, sepals, portions of stems, and several leaves.

DETAILED BOTANICAL DESCRIPTION

The following is a description of 'KORhedani' as observed in its growth in March, 2007 in a greenhouse in Jackson County, Oreg. on plants of 9 months of age. Color references are made using The Royal Horticultural Society (London, England) Colour Chart, 2001 except where common terms of color are used.

For a comparison, several physical characteristics of the rose variety 'KORneamus', a rose variety from the same inventor described and illustrated in U.S. Plant patent application Ser. No. 11/209,262, now abandoned, are compared to 'KORhedani' in Chart 1.

CHART 1

| | 'KORhedani' | 'KORneamus' |
|---|---|---|
| Petal count | 30-32 petals | 24-26 petals |
| Pistil count | Approximately 60-70. | Approximately 30-40. |
| Stamen count | Approximately 130. | Approximately 40. |

Parents:

*Seed parent.*—'an un-named seedling'.

*Pollen parent.*—'KORpolare'.

Classification:

*Botanical classification.*—*Rosa hybrida,* 'KORhedani'.

*Commercial classification.*—Miniature rose.

FLOWER AND FLOWER BUD

Blooming habit: Recurrent. Prolific.

*Flower bud.*—Size: Upon opening, 25 mm in length from base of receptacle to end of bud and 20 mm in diameter. Bud form: Long. Pointed ovoid. Bud color: As sepals first unfold, bud color is Red Group 53A. When ¼ open, the upper surface of petals is Red Group 46A, and the lower surface is Red Group 46A. Outermost petals of bud Red Group 46A. Sepals: Size: Average 30 mm long×7–8 mm wide. Shape: Sepals generally subulate. Moderately strong foliaceous appendages on three of the five sepals. Base is flat at union with receptacle. Apex long and narrow. Quantity: Five. Surface texture: Upper surface: Slightly pubescent. Lower surface: Slight to no pubescence. Lacking stipitate glands. Color Upper surface Green Group 138A. Lower surface Green Group 137B. No anthocyanin observed.

*Receptacle.*—Surface: Smooth. Color Green Group 138A. Shape: Funnel shaped. Size: 6 mm (h)×6 mm (w).

*Peduncle.*—Surface: Smooth. Length: 15 to 25 mm average length. Uppermost leaves on flowering stems consist of a single narrow straplike leaf, resembling a sepal with foliaceous appendage at distal end. Width: 3–5mm. Length: 30–40 mm. Generally held upright. Diameter: 2.0–2.5 mm average diameter. Color: Green Group 138A. Intonations of Greyed-Purple Group 183C on juvenile stems and peduncies. Strength: Strong. Borne: Singly. 6–10 buds per flowering stem.

Flower bloom:

*Fragrance.*—Light floral fragrance.

*Duration.*—Long lasting. A blooming plant with flowers having a commercial shelf life of 15 to 18 days. The blooms have a duration on the plant of approximately 12–14 days.

*Size.*—Medium for a 8–11 cm pot rose. Average flower diameter is 55 mm when open.

*Form.*—Shape of flower when viewed from the side: Upon opening, upper part: Convex. Upon opening, lower part: Flat. Open flower, upper part: Flattened convex. Open flower, lower part: Flat.

Color:

*Upon opening, petals.*—Outermost petals: Outer Side: Red Group 53B. Inner Side: Red Group 53A. Innermost petals: Outer Side: Red Group 53B. Inner Side: Red Group 53A.

*Upon opening, basal petal spots.*—Basal petal spot, outermost petals: Outer Side: Red-Purple Group 69D. Inner Side: Red-Purple Group 69D. Basal petal spot, innermost petals: Some inner petals with a Red-Purple Group 69D stripe from the basal area up to the middle zone of the outer side of the petal. At the point of attachment of petal, the color is White Group N 155B. Outer Side: Red-Purple Group 69D. Inner Side: Red-Purple Group 69D.

*After opening, petals.*—Outermost petals: Outer Side: Red Group 53B. Inner Side: Red Group 53A. Innermost petals: Outer Side: Red Group 53B. Inner Side: Red Group 53A.

*Upon opening, basal petal spot.*—Basal petal spot, outermost petals: Outer Side: Red-Purple Group 69D. Inner Side: Red-Purple Group 69D. Basal petal spot, innermost petals: Some inner petals with a near white stripe from basal area up to mid petal on the up the outer side. The color is White Group N 155B at point of attachment. Outer Side: Red-Purple Group 69D. Inner Side: Red-Purple Group 69D.

General Tonality: On open flowers Red Group 53A. No change in the general tonality at the end of the $6^{th}$ day. Afterwards, general tonality is Red Group 53B. Limited fading of the flower color.

Petals:

*Petal count.*—Double. Approximately 30–32 petals under normal conditions.

*Petal reflex.*—Petals reflex somewhat. Some of outermost petals are double reflexed.

*Petal edge.*—Slightly undulated with a point at the center of the margin.

*Petal shape.*—Apex shape is round. Shape of base is rounded.

*Petal size.*—26–30 mm long; 26–36 mm wide.

*Thickness.*—Average.

*Petal arrangement.*—Generally in a regular pattern with overlapping edges.

*Petaloids.*—Present. Average of 8 per flower. Variable in size. Many are incomplete. Petaloids are 15–20 mm long and 10–14 mm wide. Color of inner side is Red Group 53B. Color of outer side is Red Group 53B. Basal spot is Yellow-White Group 158C. Intonations in the petaloids are White Group 155A. Surface texture is smooth. Shape is linear to elliptic.

Reproductive Organs:

*Pistils.*—Average abundance. Approximately 60–70 present. Stigmas: Location: Slightly inferior in location to anthers. Color: Green-White Group 157B. Styles: Length: 50–60 mm long. Color: Uniformly Green-White Group 157B. No intonations observed.

*Stamens.*—Abundant. Approximately 130 on average and regularly arranged around the flower. Anthers: Size: 2.5–3.0 mm long. Color: Greyed-Orange Group 172D. Pollen: Generally present. Color: Greyed-Yellow Group 161D. Filaments: Color: Above: Red-Purple Group 61B. Below: Yellow-Green Group 151D. Length: Variable. 3–5 mm.

THE PLANT

*Plant growth.*—Moderately vigorous. Upright to bushy habit. When grown as an 15 cm pot plant, the average height of the plant itself is 30–35 cm and the average width is 20 cm. Stem color: Young wood: Green Group 138A. Older wood: Green Group 138A. Stem surface: Young wood: Smooth. Older wood: Smooth.

*Prickles.*—Present in limited numbers. Generally on the lower ¼ of the flowering stems. Incidence: Less than 1 per 10 cm of stem. Size: Average length: 4 mm. Color: Immature prickles: Nearly translucent. Orange-White Group 159B. Mature prickles: Greyed-Orange Group 164B. Senescing to Greyed-Orange Group 164D. Juvenile prickles may exhibit intonations of Greyed-Purple Group 183C. Shape: Deeply concave.

Leaves and leaflets. —Normally 5 leaflets on leaves positioned in the middle of the stem. Leaflets not large. Rachis is long and thin. Leaf size: 120 mm (1)×60 mm (w). Quantity: The instant variety has an average quantity of leaves and leaflets. Texture: Upper side: Semi-glossy. Nearly smooth. Lower side: Matte. Nearly smooth. Color, mature foliage: Upper Leaf Surface: Green Group 137A. Lower Leaf Surface: Green Group 138A. Color, juvenile foliage: Upper Leaf Surface: Green Group 137A. Lower Leaf Surface: Green Group 138A. Anthocyanin intonation: Present. Location: Intonations present on plants grown under high light conditions on stipules, rachis, petioles, upper side of leaflets, peduncles (limited), and on strap-like leaves below flower.

*Stipules.*—Size: 20 mm (1) — 3–4 mm (w). At distal end, 10 mm from point to point. Stipule color: Green Group 137B. On plants grown under high light conditions, intonations of Greyed-Purple Group 183C. Presence of stipitate glands: Present on margins. Margins: Serrated.

*Petiole.*—Length: 35 mm–40 mm. Diameter: 1.5 mm average diameter. Petiole color: Green Group 137A. Underneath: Green Group 138A. Anthocyanin: Present. Greyed-Purple Group 183C. Prickles: Few. Generally underneath at first set of leaflets. Stipitate glands: Present on margins.

*Petiole Rachis.*—Length: 35 mm–40 mm. Diameter: 1.5 mm average diameter. Petiole color: Green Group 137A. Underneath: Green Group 138A. Anthocyanin: Present. Greyed-Purple Group 183C. Prickles: Generally 1–2 underneath. Narrow, concave. Stipitate glands: Present on margins.

*Leaflets.*—Size: Average size of the terminal leaflet is 45 mm(l)—25–30 mm(w). Color: Upper side: Green Group 137A. Lower side: Green Group 138A. Shape: Base: Ovate. Apex: Ovate. Surface: Semi-glossy above. Matte surface below. Margins: Serrated. Texture:. Average thickness.

Hips/Seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to powdery mildew and *Botrytis* under normal growing conditions.

I claim:

1. A new and distinct variety of miniature rose plant characterized by the following combination of characteristics:

(a) forms abundant, attractive long lasting red flowers;

(b) exhibits a upright and bushy growth habit;

(c) is suited for growing in greenhouse in pots from softwood cuttings, and;

(d) exhibits durable flowers and foliage suitable for distribution in the floral industry;

substantially as herein illustrated and described.

* * * * *

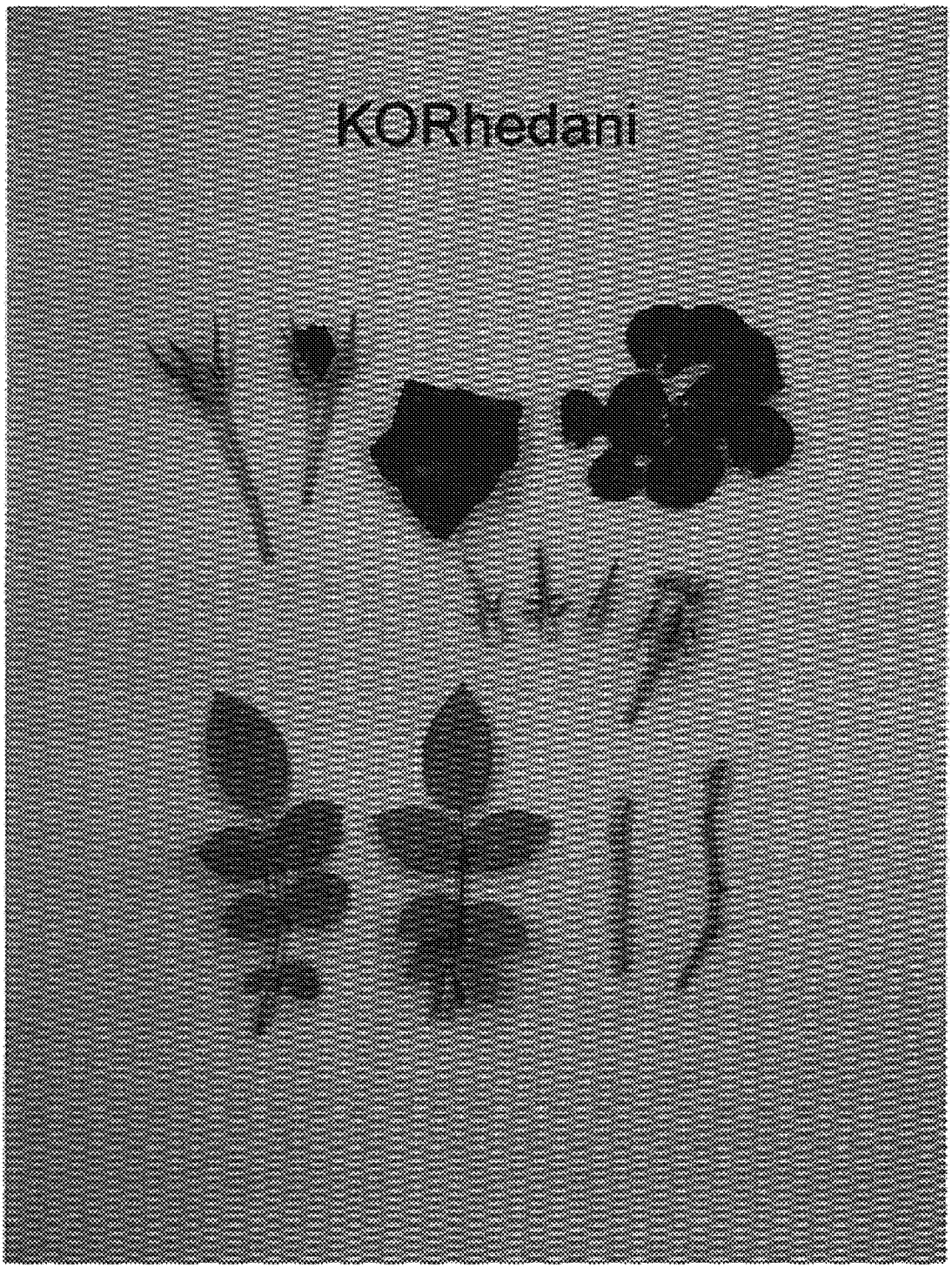
KORhedani